United States Patent
Takahashi

(10) Patent No.: US 9,044,139 B2
(45) Date of Patent: Jun. 2, 2015

(54) FLEXIBLE TUBE FOR ENDOSCOPE, AND METHOD FOR MANUFACTURING THE SAME

(75) Inventor: Nobuharu Takahashi, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 510 days.

(21) Appl. No.: 13/498,580

(22) PCT Filed: Sep. 13, 2010

(86) PCT No.: PCT/JP2010/065714
§ 371 (c)(1),
(2), (4) Date: Mar. 27, 2012

(87) PCT Pub. No.: WO2011/040215
PCT Pub. Date: Apr. 7, 2011

(65) Prior Publication Data
US 2012/0180896 A1 Jul. 19, 2012

(30) Foreign Application Priority Data
Sep. 29, 2009 (JP) ................................. 2009-224902

(51) Int. Cl.
*F16L 11/00* (2006.01)
*A61B 1/005* (2006.01)
(Continued)

(52) U.S. Cl.
CPC ............ *A61B 1/0055* (2013.01); *A61B 1/00078* (2013.01); *A61B 1/0011* (2013.01); *A61M 25/0045* (2013.01); *G02B 23/2476* (2013.01); *A61B 1/0056* (2013.01)

(58) Field of Classification Search
USPC ......................................... 138/119, 120, 137
See application file for complete search history.

(56) References Cited

U.S. PATENT DOCUMENTS 4,753,222 A * 6/1988 Morishita ..................... 600/140
5,704,401 A * 1/1998 Fukui et al. .................. 138/121
(Continued)

FOREIGN PATENT DOCUMENTS

CN 1088511 A 6/1994
CN 1925972 A 3/2007
(Continued)

OTHER PUBLICATIONS

Notification of Reason(s) for Refusal dated Feb. 8, 2013, with English translation.
(Continued)

*Primary Examiner* — James Hook
(74) *Attorney, Agent, or Firm* — McGinn IP Law Group, PLLC

(57) ABSTRACT

A flexible tube 10 is constituted of a flexible tube material 14 and a covering layer 15 of two-layers of constitution having an inner layer 17 which covers the entire peripheral surface of the flexible tube material 14 and an outer layer 18 which covers the entire peripheral surface of the inner layer 17. The covering layer 15 is two-layer molded to have the inner layer 17 and the outer layer 18, by supplying two kinds of resins into one molding die at the same time, with being overlapped each other. As resins for molding the inner layer 17 and the outer layer 18, a combination of the soft resin and the hard resin is selected to be in conditions that the difference at the 100% modulus value, which is an index of a hardness after molding, is equal to or more than 10 MPa, and that the difference of the melt viscosity in the molding temperature of 150° C. to 200° C., which is an index of the fluidity in the molten state, is equal to or less than 2500 PaS.

12 Claims, 8 Drawing Sheets

(51) Int. Cl.
  *A61B 1/00* (2006.01)
  *G02B 23/24* (2006.01)
  *A61M 25/00* (2006.01)

(56) References Cited

U.S. PATENT DOCUMENTS

| | | | |
|---|---|---|---|
| 5,928,744 A * | 7/1999 | Heilmann et al. | 428/36.6 |
| 6,053,903 A * | 4/2000 | Samson | 604/526 |
| 6,599,239 B2 | 7/2003 | Hayakawa et al. | |
| 7,169,105 B2 * | 1/2007 | Iwasaka et al. | 600/140 |
| 2002/0010386 A1 * | 1/2002 | Matsushita et al. | 600/140 |

FOREIGN PATENT DOCUMENTS

| | | |
|---|---|---|
| CN | 101416864 A | 4/2009 |
| EP | 1 780 007 A1 | 5/2007 |
| JP | 55-112505 | 8/1980 |
| JP | 62-8728 A | 1/1987 |
| JP | 08-057035 A | 3/1996 |
| JP | 2000-254235 A | 9/2000 |
| JP | 2001-161633 A | 6/2001 |
| JP | 2001-261827 A | 9/2001 |
| JP | 2009-106632 A | 5/2009 |

OTHER PUBLICATIONS

Chinese Office Action dated Dec. 26, 2013, with English translation.
Notification of Reason(s) for Refusal dated Aug. 14, 2013, with English translation.
Decision on Refusal dated Dec. 18, 2013, with English translation.
International Search Report in PCT/JP2010/040215 A1 dated Oct. 19, 2010 (English Translation Thereof).
Chinese Office Action dated Aug. 12, 2014 with an English translation thereof.
European Search Report dated Sep. 19, 2014.
Chinese Office Action dated Dec. 25, 2014 with English Translation.

* cited by examiner

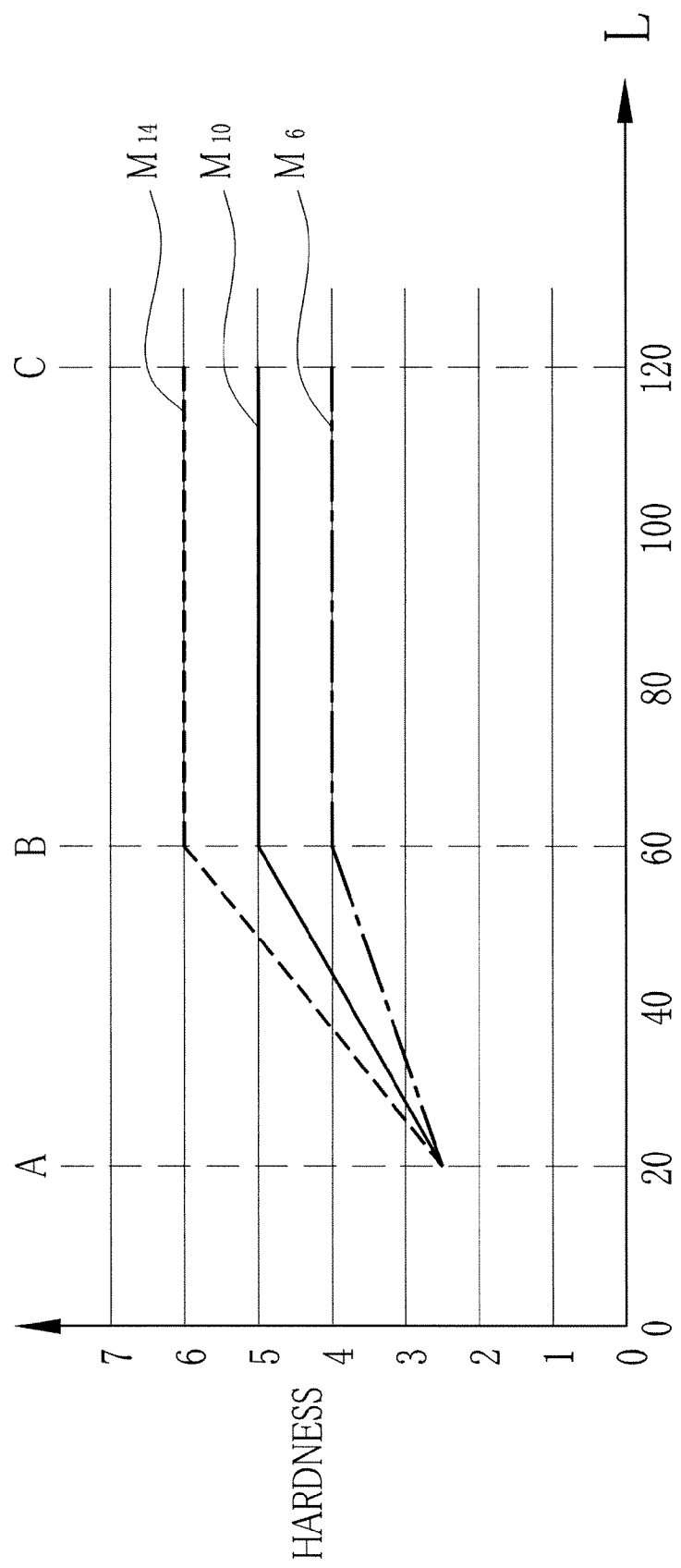

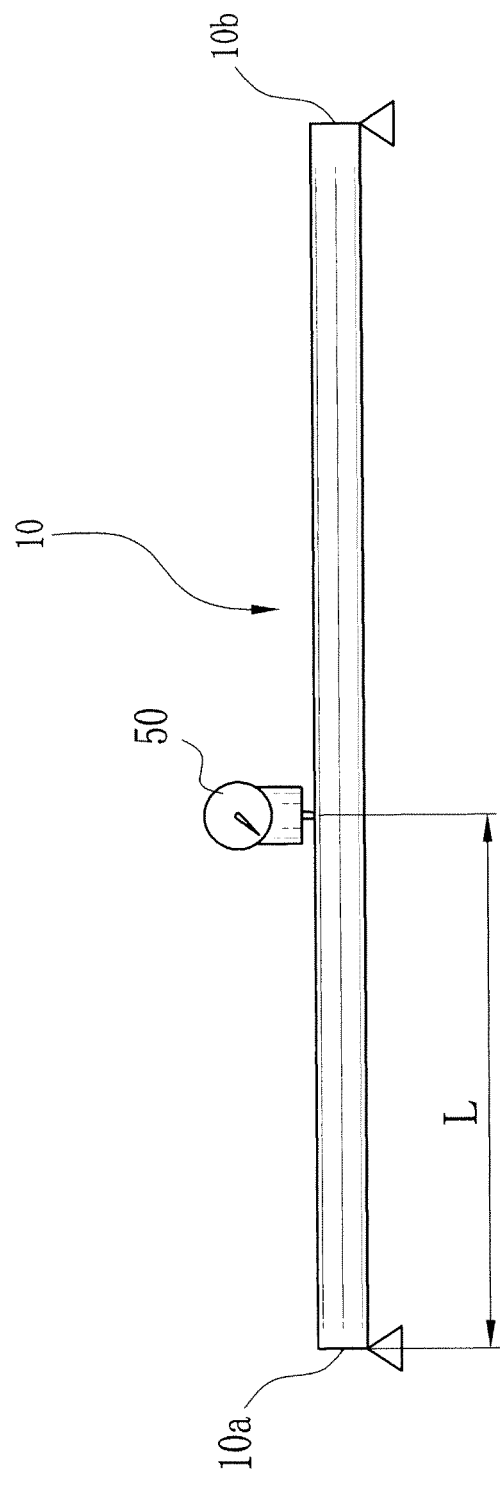

FLEXIBLE TUBE FOR ENDOSCOPE, AND METHOD FOR MANUFACTURING THE SAME

TECHNICAL FIELD

The present invention relates to a flexible tube for endoscope, in which a covering layer is multi-layer molded of plural kinds of resins, and a method for manufacturing the same.

BACKGROUND ART

An endoscope for medical use, which is for imaging the inside of a living body cavity, is known. A flexible tube is a main part of an insert section of the endoscope, which is inserted into the inside of a living body cavity, and is constituted of a helical coil made of a metal ribbon wound helically, and a covering layer made of resin such as a urethane resin on the periphery of a tubular net. The covering layer is over-molded by extrusion, on the periphery of a flexible tube material formed by covering the helical coil with a tubular net. The flexible tube is expected to have high flexibility (to be soft) at a distal end for better insertability into the living body cavity, and low flexibility (hard) at a proximal end for better operatability.

For this reason, it is known that a covering layer is two-layer molded to have an inner layer and an outer layer whose hardness are different from each other, and that, though the outside diameter of the covering layer is constant throughout the whole length, the flexibility of flexible tube in the axial direction is changed (a difference is made in the hardness) by varying a thickness ratio between the inner layer and the outer layer in the axial direction of flexible tube (patent documents 1 and 2).

As one of the methods to two-layer mold the covering layer, the two-layer simultaneous molding method, in which the inner layer and the outer layer constituting the covering layer are molded at the same time, are known. In the two-layer simultaneous molding method, two kinds of resins are heated at a respective appropriate temperature in two extrusion sections provided in an extrusion machine, to be in a molten condition. And two kinds of resins in the molten condition join before being supplied into a molding die in which a molding passage where flexible tube materials from each extrusion section pass is formed, and are supplied to the molding die in the state that two kinds of resins are overlapped. In this way, the covering layer of two-layers constitution covers the periphery of the flexible tube material.

PRIOR ART DOCUMENTS

Patent Documents

Patent Document 1: Japanese Utility Model Laid-Open Application Publication No. 55-112505
Patent Document 2: Japanese Patent Laid-Open Application Publication No. 62-8728

SUMMARY OF INVENTION

Problems to be Solved by the Invention

It is correlative between a temperature to make resin a melt viscosity (a value to express fluidity of the resin) suitable for molding and a hardness of the resin which is cooled off and stiffened after molding, and with the resin which is high in the hardness after the molding, a temperature to make it the melt viscosity suitable for molding is high, and the temperature to do so is low with the resin that the hardness after the molding is low. Therefore, when two-layer molding the two kinds of resins having different hardness, which are the hard resin and the soft resin, a heating temperature is set in each extrusion section to make each resin the melt viscosity suitable for molding.

However, in the two-layer simultaneous molding method, because two kinds of resins are finally supplied to one molding die at the same time, they are exposed to the same temperature in the molding die. Because a difference occurs to the melt viscosities of two kinds of resins at the same temperature, inconveniences as described below occur.

When the inside temperature (molding temperature) of the molding die is set to match the hard resin which is high in the hardness after the molding, although the hard resin becomes the appropriate melt viscosity, but the melt viscosity of the soft resin, having low hardness after the molding, becomes very low, and it becomes in a state that the resin is very soft (the state that fluidity is too high).

If the fluidity of the soft resin becomes very high, on a boundary of the hard resin and the soft resin flowing with being overlapped in the molding die, a phenomenon that a part of the hard resin (whose melt viscosity is high) invades the inside of the soft resin (whose melt viscosity is low) occurs (the invading phenomenon). When the invading phenomenon occurs, a decline of the molding precision occurs, which is such as disappearing of the uniformity of the thickness of each layer in the circumferential direction, or each layer not becoming the intended thickness. In addition, when the melt viscosity is very low (the fluidity is very high), because the resin penetrates into a gap between a mesh pipe and a helical coil constituting the flexible tube material, this reason also decreases the molding precision.

Conversely, when the molding temperature in the two-layer molding is set to match the soft resin, since the melt viscosity of the hard resin is not lowered and the appropriate fluidity is not obtained, a decline of the molding precision occurs, which is such as the thickness in the circumference direction being ununiformed, or the hard resin layer not becoming the intended thickness. The decline of the molding precision becomes more remarkable when the difference in the melt viscosities at the same molding temperature between the hard resin and the soft resin becomes larger (the difference in the hardness between the hard resin and the soft resin becomes larger).

The melt viscosity difference between two kinds of resins in the molding temperature should be small to improve molding precision. However, that, the melt viscosity difference in the molding temperature is small, means that the difference in the hardness after the molding is small. When the difference in the hardness is small, even if the thickness ratio of the inner layer to the outer layer changes, there is a problem that the hardness difference that is necessary between the distal side and the proximal side is not secured.

Therefore, on the manufacturing ground, it is required that measures to secure both good molding precision and necessary hardness difference. The above-mentioned patent documents land 2 do not consider such problems at all, and do not give any statement or suggestion about the relation between the hardness after the molding and the melt viscosity at the molding temperature in two kinds of resins.

The present invention was made in consideration of the circumstances mentioned above, in order to provide a flexible tube for endoscope which has a covering layer which can secure both good molding precision and hardness difference that is necessary between the distal side and the proximal side, and a method for manufacturing the same.

Means for Solving the Problems

To achieve the above objects, a flexible tube for endoscope of the present invention includes a pipe-shaped flexible tube material and a covering layer of a multi-layered constitution, in which the entire peripheral surface of the axis circumference of the flexible tube material is covered with a plurality of layers molded by extrusion molding, in which a plurality of kinds of resins each having different molten condition each other is supplied in an overlapped manner to one molding die to which the flexible tube material is inserted, and is characterized in that the resin used for molding of the first layer of the covering layer and the resin used for molding of the second layer that contacts the first layer is in conditions that the difference at the 100% modulus value, which represents a hardness after molding, is equal to or more than 10 MPa, and that the difference of the melt viscosity in the temperature of 150° C. to 200° C., where the resins are molten for molding, is equal to or less than 2500 PaS.

It is preferable that the first layer of the covering layer is an inner layer which covers the entire peripheral surface of the axis circumference of the flexible tube material, and the second layer is an outer layer which contacts the inner layer and covers the entire peripheral surface of the axis circumference of the inner layer, and thickness ratio of each of the inner layer and the outer layer to the overall thickness of the covering layer are varied along the axial direction of the flexible tube material.

It is preferable that the resin used for molding the inner layer is a soft resin, and the resin used for molding the outer layer is a hard resin. It is preferable that the flexible tube material and the covering layer are incorporated in an insert section of an endoscope, a thickness ratio between the inner layer and the outer layer is 1:9 at a proximal end of the insert section, the thickness ratio between the inner layer and the outer layer is 9:1 at a distal end of that, and the thickness ratio reversely changes between the both ends. It is preferable that the thickness of the covering layer is 0.2 mm to 1.0 mm.

The present invention, in relation to a method for manufacturing a flexible tube for endoscope including a pipe-shaped flexible tube material and a covering layer of a multi-layered constitution, in which the entire peripheral surface of the axis circumference of the flexible tube material is covered with a plurality of layers molded by extrusion molding, in which a plurality of kinds of resins each having different molten condition each other is supplied in an overlapped manner to one molding die to which the flexible tube material is inserted, is characterized in that the resin used for molding of the first layer of the covering layer and the resin used for molding of the second layer that contacts the first layer is in conditions that the difference at the 100% modulus value, which represents a hardness after molding, is equal to or more than 10 MPa, and that the difference of the melt viscosity in the temperature of 150° C. to 200° C., where the resins are molten for molding, is equal to or less than 2500 PaS.

It is preferable that the first layer of the covering layer is an inner layer which covers the entire peripheral surface of the axis circumference of the flexible tube material, and the second layer is an outer layer which contacts the inner layer and covers the entire peripheral surface of the axis circumference of the inner layer, and thickness ratio of each of the inner layer and the outer layer to the overall thickness of the covering layer are varied along the axial direction of the flexible tube material while molding the covering layer.

It is preferable that the resin used for molding the inner layer is a soft resin, and the resin used for molding the outer layer is a hard resin. It is preferable that the flexible tube material and the covering layer are incorporated in an insert section of an endoscope, a thickness ratio between the inner layer and the outer layer is made to be 1:9 at a proximal end of the insert section, the thickness ratio between the inner layer and the outer layer is made to be 9:1 at a distal end of that, and the thickness ratio is reversely changed between the both ends while molding the covering layer.

Effect of the Invention

According to the present invention, since a resin used for molding of the first layer of the covering layer and a resin used for molding of the second layer that contacts the first layer is in conditions that the difference at the 100% modulus value, which represents a hardness after molding, is equal to or more than 10 MPa, and that the difference of the melt viscosity in the temperature of 150° C. to 200° C., where the resins are molten for molding, is equal to or less than 2500 PaS, the flexible tube for endoscope, which can secure both the good molding precision and the necessary hardness differences between the distal end side and the proximal end side of for example the insert section for endoscope, can be provided.

BRIEF DESCRIPTION OF DRAWINGS

FIG. 7 is a graph showing hardness distributions along the axial direction of flexible tubes varying at 100% modulus value.

FIG. 8 is an explanatory drawing illustrating a method for measuring the hardness distribution of the flexible tube.

MODE FOR CARRYING OUT THE INVENTION

Figure 1:
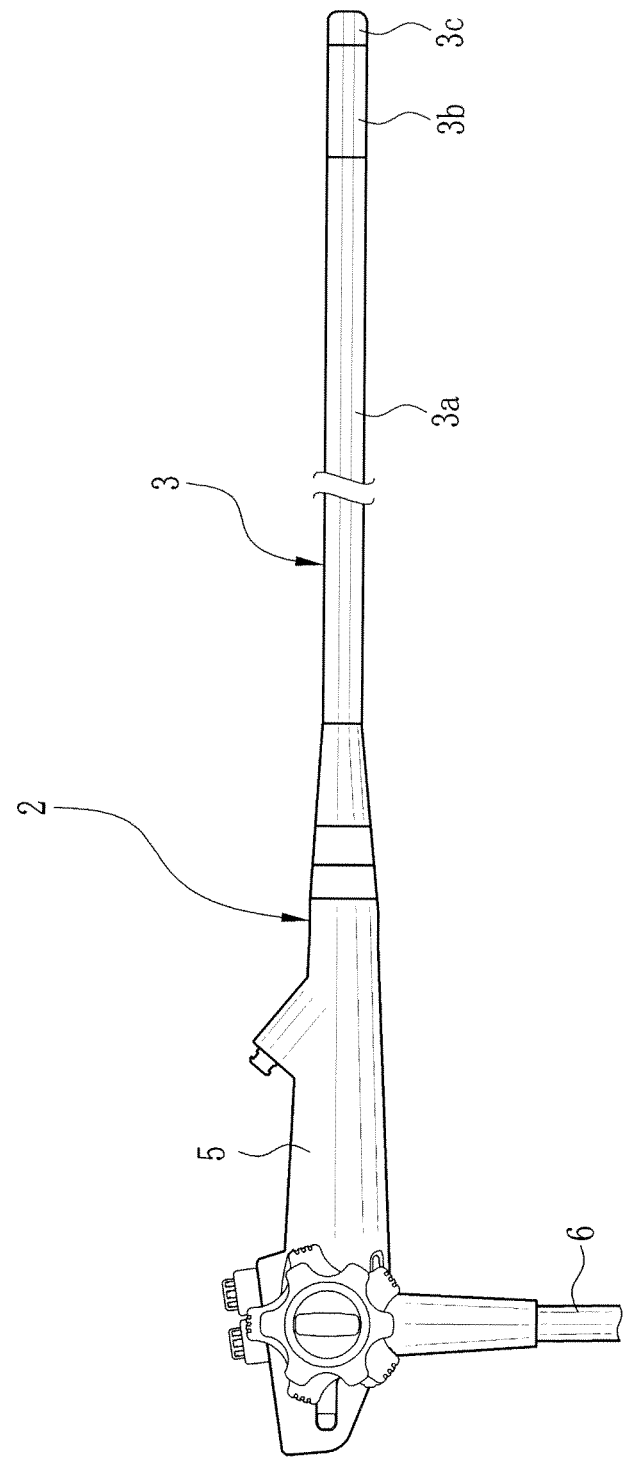
FIG. 1 is an external view illustrating a constitution of an electronic endoscope.

As in FIG. 1, which illustrates an electronic endoscope where a flexible tube according to the present invention is incorporated in, an electronic endoscope 2, which is widely used for a medical application, is constituted of an insert section 3 to be introduced into a living body cavity, a handling section 5 coupled to a base end of the insert section 3, and a universal cord 6 connected to a processor unit and a light source unit.

The insert section 3 is constituted of a flexible tube unit 3a which is connected to a handling section 5, an angle section 3b which is connected to the flexible tube unit 3a, and a distal portion 3c which is connected at the end and contains an image sensor (not illustrated) for imaging an internal body part. The flexible tube unit 3a which occupies most of the length of the insert section 3 has flexibility for almost full length, especially, a part which will be inserted inside a living body cavity or so on has a structure being more flexible.

Figure 2:
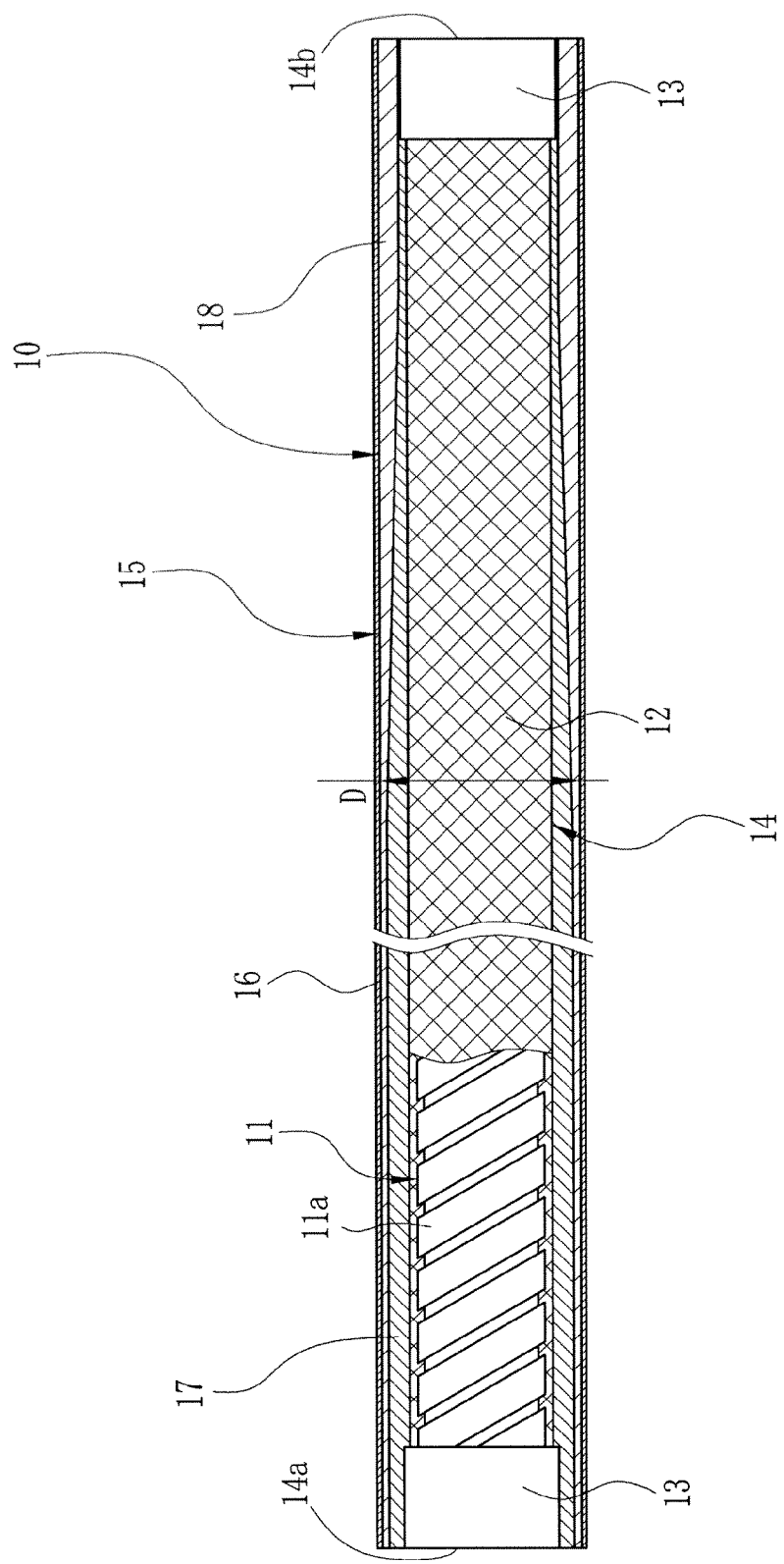
FIG. 2 is a partial cross sectional view illustrating a schematic constitution of a flexible tube.

A flexible tube 10 (flexible tube for endoscope) which constitutes the flexible tube unit 3a, as illustrated in FIG. 2, has a flexible tube material 14, in which a tubular net 12 made of braided metal wires is layered on a helical coil 11 formed by helically wound a metal ribbon 11a at the most inner side and metal rings 13 are fitted into both ends, and has the constitution that the periphery of the flexible tube material 14 is covered by a covering layer 15 made of resin. In addition, on the outside of the covering layer 15, a coating film 16 which contains for example fluorine having chemical resistance is coated. Only one level of the helical coil 11 is illustrated in the figure, but it may be constituted to have two-layers coaxially overlapped. Note that the covering layer 15 and the coating film 16 are drawn to be thicker in comparison with the diameter of the flexible tube material 14, in order to definitely illustrate the laminar structure.

The covering layer 15 covers the periphery of the flexible tube material 14. The covering layer 15 has a two-layers constitution in which an inner layer 17, which covers all peripheral surfaces of the axis circumference of the flexible tube material 14, and an outer layer 18, which covers all peripheral surfaces of the axis circumference of the inner layer 17, are overlapped. The soft resin is used as the material of the inner layer 17, and the hard resin is used as the material of the outer layer 18.

The covering layer 15 is formed at approximately uniform thickness in the longitudinal direction (the axial direction) of the flexible tube material 14. The thickness of the covering layer 15 is for example 0.2 mm to 1.0 mm, and the outer diameter D of the flexible tube 10 is for example 11 to 14 mm.

The thickness of each of the inner layer 17 and the outer layer 18 is formed such that the thickness ratio of each of the layers 17 and 18 to the overall thickness of the covering layer 15 changes along the axial direction of the flexible tube material 14. Specifically, the thickness of the inner layer 17 is bigger than the thickness of the outer layer 18 in the overall thickness of the covering layer 15 at the side of one end 14a (the distal side) of the flexible tube material 14 where the angle section 3b is attached, then the thickness of the inner layer 17 gradually decreases from the one end 14a towards the side of another end 14b (the proximal side) where the handling section 5 is attached, and then the thickness of the outer layer 18 becomes bigger than the thickness of the inner layer 17, at the side of the other end 14b.

At the both ends 14a and 14b, the thickness ratio between the inner layer 17 and the outer layer 18 becomes maximum, it is 9:1 at the end 14a, and it is 1:9 at the other end 14b. Between the both ends 14a and 14b, the thickness ratio between the inner layer 17 and the outer layer 18 reversely changes. In this way, in the flexible tube 10, the difference occurs in the hardness between the end 14a side and the other end 14b side, and the flexibility changes in the axial direction so that the end 14a side becomes soft, and the other end 14b side becomes hard.

Note that it is preferable that the thickness ratio between the inner layer 17 and the outer layer 18 is from 1:9 to 9:1 as the above example. In a case (e.g., 0.5:9.5) beyond this ratio, it is difficult to control an extruding amount of the resin of the thinner one, and a molding irregularity is easy to occur.

As the soft resin and the hard resin to use for the inner layer 17 and the outer layer 18, as described later, two kinds of resins, in which the difference in the 100% modulus value that is an index to express the hardness after the molding is higher than 10 MPa, and the difference in the melt viscosity in the molding temperature of 150° C. to 200° C. that is an index to express the fluidity of the resin in the molten condition is lower than 2500 PaS, are used. Therefore, in the covering layer 15 consisting of the inner layer 17 and the outer layer 18, both of good molding precision and hardness difference which is necessary in the distal side and the proximal side are secured.

Figure 3:
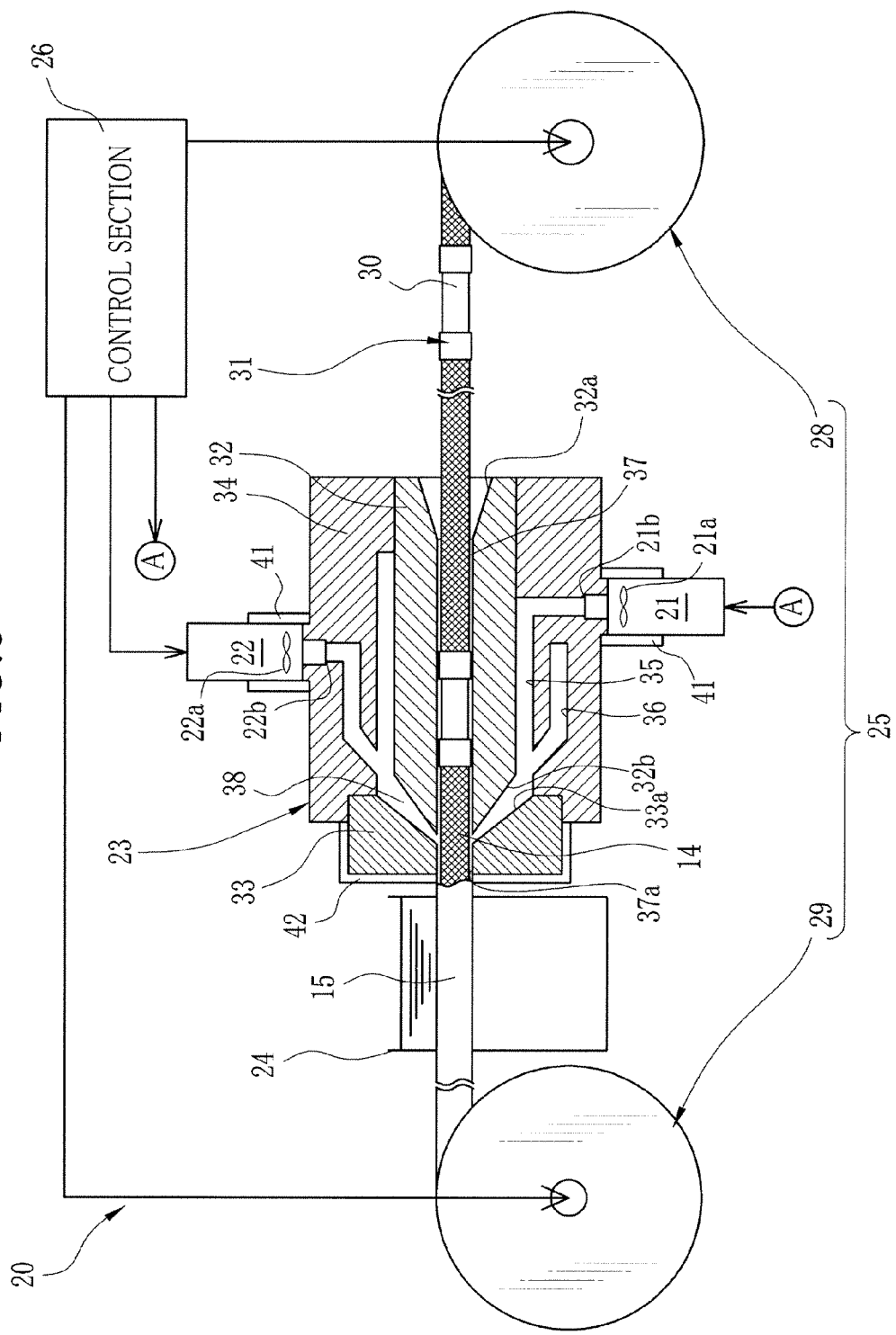
FIG. 3 is a block diagram schematically illustrating a constitution of a manufacturing apparatus for the flexible tube for endoscope.

At first, in the following, a manufacturing method of the flexible tube 10 (a molding method of the covering layer 15) will be described. In FIG. 3, which illustrates a constitution of a continuous extrusion apparatus 20 for forming the covering layer 15, the continuous extrusion apparatus 20 is provided with known extrusion sections 21, 22 including a hopper, a screw 21a or 22a, and the like, a head section 23 to form the covering layer 15 by coating molding on the periphery of the flexible tube material 14, a cooling section 24, a feeding section 25 which transports an assembled flexible tube material 31 to the head section 23, and a control section 26 which controls these.

The feeding section 25 is constituted of a feed drum 28 and a winding drum 29, and the assembled flexible tube material 31 which is formed by connecting the plurality of the flexible tube materials 14 with use of joint members 30 is wound around the feed drum 28. After wound around the feed drum 28, the assembled flexible tube material 31 is drawn sequentially, passes through the head section 23 where the covering layer 15 is molded and the cooling section 24 where the covering layer 15 after molded is cooled, and is wound by the winding drum 29. A transportation speed to transport the assembled flexible tube material 31 is changed by a rotating speed of the feed drum 28 and the winding drum 29, which is controlled by the control section 26.

Figure 4:
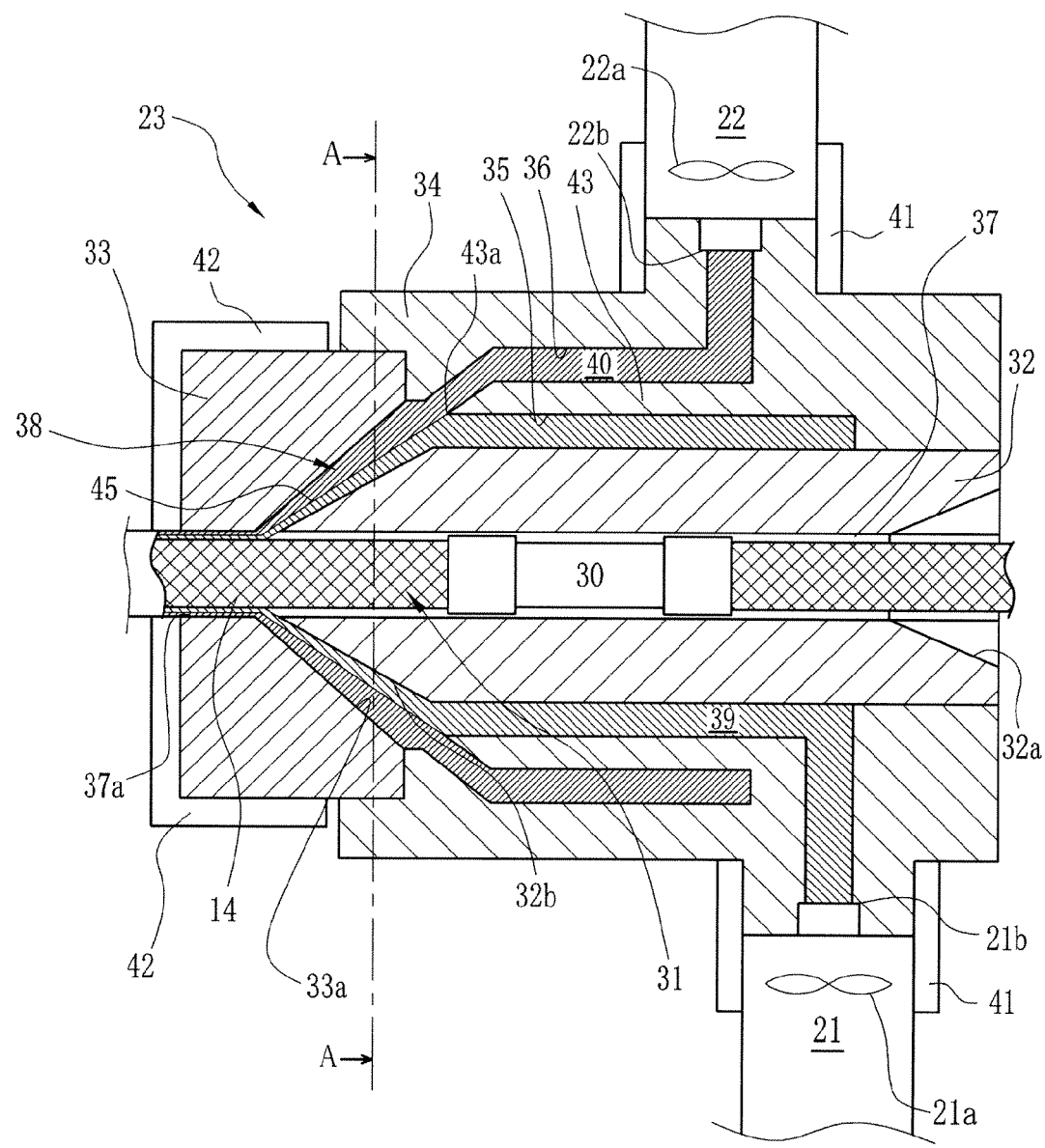
FIG. 4 is an essential part cross sectional view illustrating a constitution of a head section.

As illustrated in FIG. 3 and FIG. 4, the head section 23 is constituted of a nipple 32, a dice 33 and a support 34 which supports these in a stational manner. In the support 34, gates 35, 36 are formed to send the soft resin 39 and the hard resin 40 in the molten condition, which are pushed out from the extrusion sections 21, 22 (refer also to FIG. 5), to a resin passage 38.

A molding passage 37 is formed in each of the nipple 32 and the dice 33 as the molding die to penetrate each approximal center. The molding passage 37 is the passage where the assembled flexible tube material 31 transported in the axial direction by the feeding section 25 passes, and a cross-sectional shape at right angles to the axial direction is a circle (refer to FIG. 5). The molding passage 37 is connected to a discharge opening, which corresponds to the down-stream end of the resin passage 38, and the soft resin 39 and the hard resin 40 in the molten condition are supplied to the molding passage 37 from the resin passage 38.

The resin passage 38 is formed by the space between the nipple 32 and the dice 33. At the left-side end in the figure of the nipple 32, a conical projection 32b, which forms the resin passage 38 with a conical recess 33a in the right-side end of the dice 33, is formed. In addition, a conical recess 32a is formed to be connected to the right-side end in the figure of the molding passage 37 and to guide the insertion of the assembled flexible tube material 31.

An outlet vent 37a of the molding passage 37 is formed in the dice 33. The assembled flexible tube material 31, on which the covering layer 15 is molded, is transported to the cooling section 24 through the outlet vent 37a. As coolant such as water is in the cooling section 24, the covering layer 15 is cooled to be hardened while traveling through the coolant. Instead of above, coolant, air or the like may be blown to the covering layer 15 to cool it.

The resin passage 38 is placed outside of the molding passage 37, and a cross-sectional shape at right angles to the axial direction of the molding passage 37 is a circle concentric with the molding passage 37. A discharge opening of the resin passage 38 is connected to whole circumference along the circumferential direction of the molding passage 37. Therefore, toward whole circumference of the assembled flexible tube material 31 passing the discharge opening of the resin passage 38, the soft resin 39 and the hard resin 40 in the molten condition are discharged.

The extrusion sections 21, 22 have discharge openings 21b, 22b respectively coupled to the gate 35, 36 of the head section 23, and push to supply the soft resin 39 and the hard resin 40 in the molten condition, to be the materials of the inner layer 17 and the outer layer 18, toward the molding passage 37 of the head section 23 through the resin passage 38. Since each number of revolutions of the screws 21a, 22a is controlled by the control section 26, each quantity of the soft resin 39 and the hard resin 40 in the molten condition, discharged from the extrusion sections 21, 22, is regulated.

The extrusion sections 21, 22 and the dice 33 are respectively provided with heating sections 41, 42. The heating section 41 is provided to surround a part of the extrusion sections 21, 22 and the gates 35, 36. The heating section 41 is for example a heater constituted of heating wires, and is provided to each of the extrusion sections 21, 22. The soft resin 39 and the hard resin 40 pushed out from the extrusion sections 21, 22 are heated by each heating section 41 so that each becomes the appropriate melt viscosity. The heated soft resin 39 and hard resin 40 are sent to the resin passage 38, in the molten condition.

The heating section 42 is provided to surround the periphery and the tip surface of the dice 33. The heating section 42 is a heater constituted of heating wires as same as the heating section 41, and heats inside of the dice 33, that is, inside the molding passage 37 and the resin passage 38 to predetermined molding temperature. The molding temperature is set in the range of 150° C. to 200° C. The soft resin 39 and the hard resin 40 are sent to the resin passage 38 heated to the molding temperature mentioned above, and are supplied to the molding passage 37 through the resin passage 38.

Although each temperature of the soft resin 39 and the hard resin 40 becomes a high temperature by heating-temperature control of the heating sections 41, 42, in addition, when each number of revolutions of the screws 21a, 22a becomes higher, each temperature of the soft resin 39 and the hard resin 40 becomes also higher, and each fluidity increases. Each molding thickness of the inner layer 17 and the outer layer 18 is adjusted by changing each discharge amount of the soft resin 39 and the hard resin 40 in the molten condition, while the transportation speed of the assembled flexible tube material 31 is kept constant.

Both the gates 35, 36, whose center is at the molding passage 37, are positioned outside of the molding passage 37, and the gate 36 is located outside of the gate 35. The gates 35, 36 are approximately cylindrical passages whose cross-section at right angles to the axial direction of the molding passage 37 has a circular shape. In the gates 35, 36, a downstream end of the feeding direction of the soft resin 39 and the hard resin 40 is connected to an upstream end of the resin passage 38. This connection part becomes a merging section where the soft resin and the hard resin come together. Between the gates 35, 36, a separation section 43 is provided to separate the both.

In the separation section 43, an edge 43a is provided in the merging section, and separates the gates 35, 36 in the upstream side of the merging section. The soft resin 39 and the hard resin 40 sent from the each gate 35, 36 pass the edge 43a and come together. The edge 43a has a cross-section that is parallel to the axial direction, whose shape is tapered toward the tip, to let two kinds of resins come together.

Figure 5:
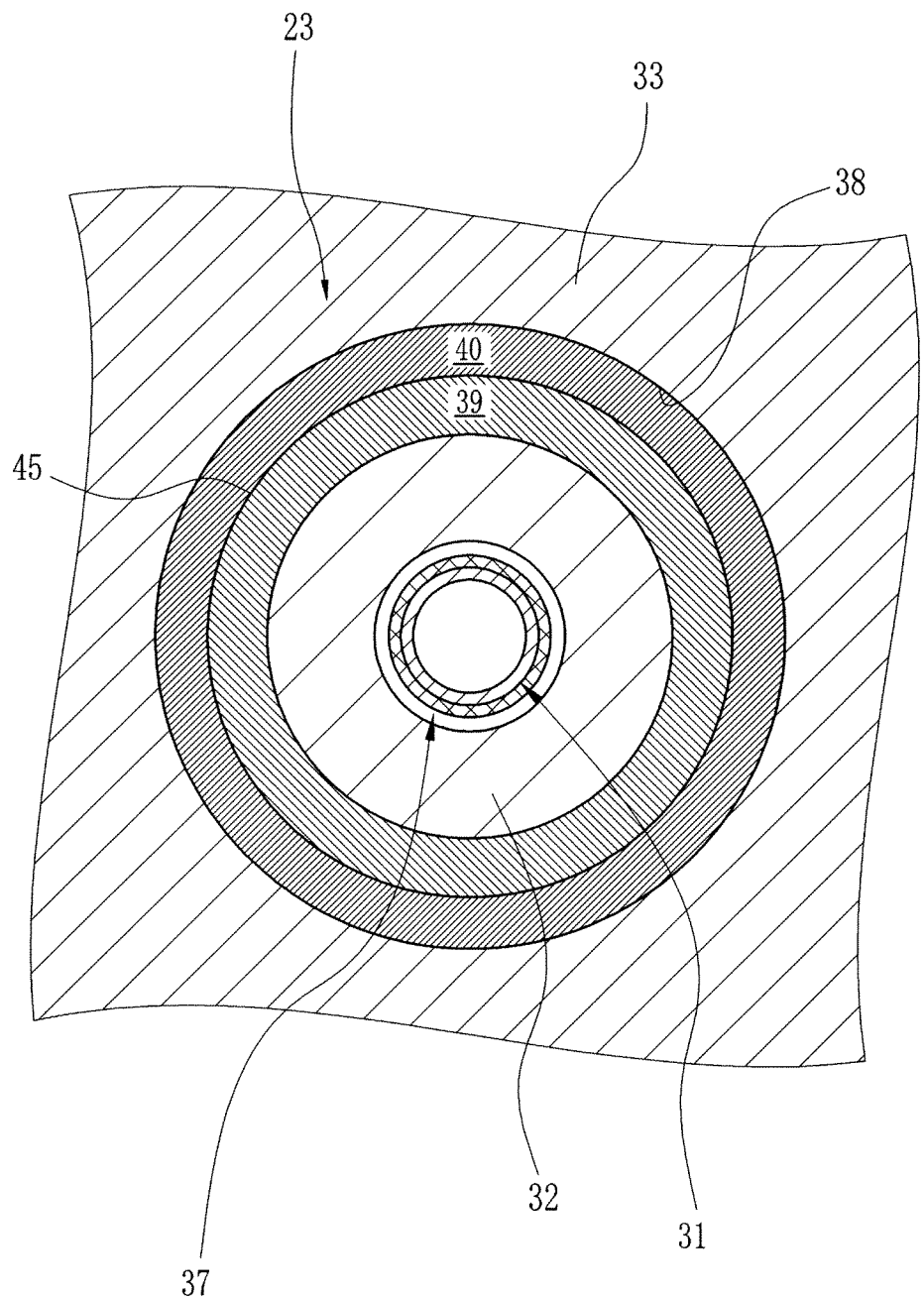
FIG. 5 is a cross sectional view along an A-A line of FIG. 4.

In the merging section where the soft resin 39 and the hard resin 40 come together, the soft resin 39 in the molten condition supplied from the gate 35 becomes inside, and the hard resin 40 in the molten condition supplied from the gate 36 becomes outside, when they come together to be overlapped. As illustrated in FIG. 4 and FIG. 5, the soft resin 39 and the hard resin 40 flow through the resin passage 38 while they are overlapped. Note that a numeral 45 in FIG. 4 and FIG. 5 shows a boundary of the soft resin 39 and the hard resin 40 in the resin passage 38. The soft resin 39 and the hard resin 40 are discharged toward the whole circumference of the assembled flexible tube material 31 from the discharge opening which is connected to the whole circumference of the molding passage 37 in the circumferential direction, with keeping the state that they are overlapped. In this way, the covering layer 15 consisting of two-layers of the inner layer 17 and the outer layer 18 is molded.

It will be described that a process to mold the covering layer 15 on the assembled flexible tube material 31 in the continuous extrusion apparatus 20 of the constitution mentioned above. When the continuous extrusion apparatus 20 performs the forming step, the soft resin 39 and the hard resin 40 in the molten condition are pushed out from the extrusion sections 21, 22 to the head section 23, and the feeding section 25 is activated to feed the assembled flexible tube material 31 to the head section 23.

At this time, the extrusion sections 21, 22 always push the soft resin 39 and the hard resin 40 to supply them to the head section 23, and the soft resin 39 and the hard resin 40 pushed from the extrusion sections 21, 22 to the gate 35, 36 join together through the edge 43a, and are supplied to the molding passage 37 through the resin passage 38, in the state that they are overlapped. In this way, the covering layer 15 of two-layers, in which the outer layer 18 of the hard resin 40 is overlapped with the inner layer 17 of the soft resin 39, is formed.

The assembled flexible tube material 31 is a plurality of the flexible tube materials 14 connected together, and the covering layer 15 is molded continually on the plural flexible tube materials 14, while they are traveling through the molding passage 37. When molding the covering layer 15 from the one end 14a side (the distal side) to the other end 14b side (the proximal side) of one flexible tube material 14, right after having started the discharge of the resins by the extrusion sections 21, 22, thickness of the inner layer 17: thickness of the outer layer 18 becomes 9:1, then the thickness ratio of the outer layer 18 gradually increases between the one end 14a side and the other end 14b side of the flexible tube material 14, and then at the other end 14b side of the flexible tube material 14, thickness of the inner layer 17: thickness of the outer layer 18 becomes 9:1. To accomplish the above, the control section 26 controls discharging amount of the resin from the extrusion sections 21, 22.

Because the joint member 30 is the connection part of the two flexible tube materials 14, the control section 26 is used for a change of the discharge amount from the extrusion sections 21, 22. Specifically, the control section 26 changes the discharge amounts of the extrusion sections 21, 22 from the thickness ratio in the other end 14b side of one flexible tube material 14 (the proximal side) to the thickness ratio in the one end 14a side of the next flexible tube material 14 (the distal side).

And when the covering layer 15 is molded from the one end 14a side to the other end 14b side of the next flexible tube material 14, correspondingly, the extrusion sections 21, 22 are controlled so that the thickness of the outer layer 18 gradually grows from the one end 14a side towards the other end 14b side. After that the same process is repeated to mold the covering layer 15 on the whole of the assembled flexible tube material 31.

The assembled flexible tube material 31 where the covering layer 15 is molded up to the proximal end is removed from the continuous extrusion apparatus 20, and the joint members 30 are removed from the flexible tube materials 14 to disassemble into the each flexible tube material 14. Then, for the disassembled flexible tube material 14, the coating film 16 is coated on the covering layer 15, and the flexible tube 10 is completed. The completed flexible tube 10 is transported to the assembly process of the electronic endoscope 2.

As described above, the flexible tube 10 of the present invention has the covering layer 15 having good molding precision and hardness difference to be required between the distal side and the proximal side. In the present invention, as materials of the inner layer 17 and the outer layer 18, two kinds of resins, between which a difference at the 100% modulus value which is an index to express the hardness after the molding is equal to or more than 10 MPa, and a difference of the melt viscosity in the molding temperature of 150° C. to 200° C. which is an index to express the fluidity of the resin in the molten condition is equal to or less than 2500 PaS, are used.

For example, a pair of the resins which can meet these two conditions is a combination of a resin chosen from polyurethane resin and a resin chosen from polyester resin. In this case, the soft resin 39 is chosen from polyurethane resin, and the hard resin 40 is chosen from polyester resin. Polyurethane resin and polyester resin have a large difference in the 100% modulus value, and a small difference in the melt viscosity in the molding temperature of 150° C. to 200° C.

In addition, from polyurethane resin, a combination of resins meeting the above two conditions can be selected. In addition, not only this, a combination of resins meeting the above conditions can be selected from synthetic resins such as high-molecular compounds other than polyurethane resin and polyester resin.

In the following, the difference in the modulus value and the difference in melt viscosity at the molding temperature will be described in detail. At first, it will be described with reference to FIG. 6A and FIG. 6B, that the condition to get good molding precision is that the melt viscosity difference in the molding temperature of 150° C. to 200° C. is equal to or less than 2500 PaS.

Figure 6A:
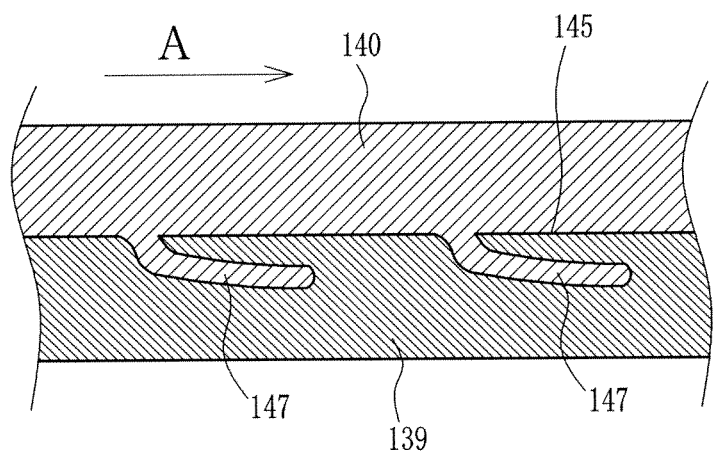
FIG. 6A is an explanatory drawing to explain a comparative example in which a melt viscosity difference in the molding temperature is large.
Figure 6B:
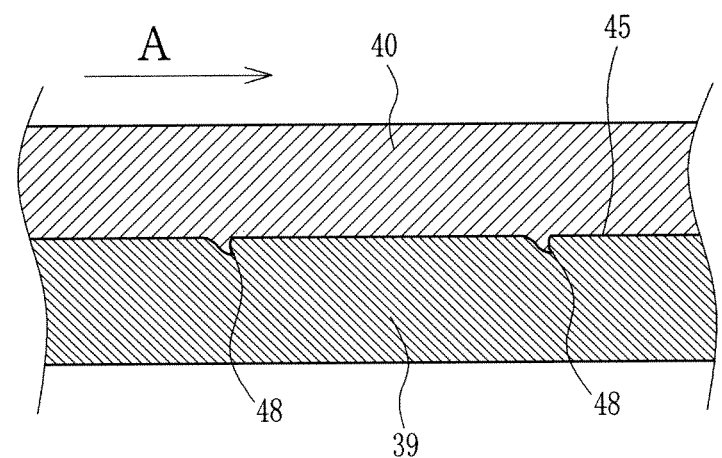
FIG. 6B is an explanatory drawing to explain an embodiment in which a melt viscosity difference is smaller than the comparative example.

FIG. 6A and FIG. 6B illustrates the state when the soft resin 39 and the hard resin 40 supplied from the gates 35, 36 are overlapped at the merging section and are heated to the molding temperature of 150° C. to 200° C. and then is transported from the resin passage 38 to the molding passage 37. FIG. 6A illustrates a soft resin 139 and a hard resin 140 which are the comparative example that the melt viscosity difference in 150° C. to 200° C. of the molding temperature does not meet the above condition (more than 2500 PaS), and FIG. 6B illustrates the soft resin 39 and the hard resin 40 of the present invention that the melt viscosity difference in 150° C. to 200° C. of the molding temperature meets the above condition (equal to or less than 2500 PaS).

Concretely, the soft resin 139 and the hard resin 140 illustrated in FIG. 6A have the melt viscosities of 500 PaS and 6000 PaS each in the molding temperature of 150° C. to 200° C., and the melt viscosity difference of 5500 PaS. In this case, the melt viscosity of the soft resin 139 is very low (soft) for the hard resin 140. And if the melt viscosities are different, since the difference of the drift velocities between the soft resin 139 and the hard resin 140 become large, a part of the hard resin 140 greatly invades into the inside of the soft resin 139 in the vicinity of a boundary 145. A numeral 147 is an invading part of the hard resin 140 into the soft resin 139, and an arrow A illustrates a flow direction of the hard resin 140.

Since this invading part 147 is large, and a large irregularity occurs in the vicinity of the boundary 145, as for the inner layer 17 and the outer layer 18, each thickness in the circumferential direction becomes uneven and does not become the intended thickness. Because the thickness of the covering layer 15 is about 0.2 mm to 1.0 mm, the influence that such invading part 148 gives in each thickness of the inner layer 17 and the outer layer 18 is large.

On the other hand, the soft resin 39 and the hard resin 40 of the present invention illustrated in FIG. 6B have the melt viscosities of 500 PaS and 3000 PaS each in the molding temperature of 150° C. to 200° C., and satisfy the condition that the melt viscosity difference in 150° C. to 200° C. of the molding temperature is equal to or less than 2500 PaS.

In case of such the soft resin 39 and the hard resin 40, since the melt viscosity difference and the flow speed difference are small, invading amount of the hard resin 40 to the soft resin 39 is small, as illustrated in FIG. 6B. A numeral 48 is an invading part of the hard resin 40 into the soft resin 39 at the boundary 45. Although this invading part 48 causes minor irregularities in the vicinity of the boundary 45, the degree of the invading is small so that it can be disregarded in relation to the thickness of the each layer. From the above, when the soft resin 39 and the hard resin 40, which satisfy the condition that the melt viscosity difference in 150° C. to 200° C. of the molding temperature is equal to or less than 2500 PaS, are used, good molding precision can be obtained.

Then, it will be described with reference to FIG. 7 and FIG. 8, that the condition to make the hardness difference necessary for the covering layer 15 between the distal side and the proximal side is that the difference in the 100% modulus value is higher than 10 MPa. The modulus value is a stress per unit area when a constant stretch is given, and a material having a higher modulus value is harder. And the 100% modulus value is a stress per unit area (a stress given to a stretching direction/a cross section at right angles to the stretching direction) when the 100% stretch is given to a material (in other words, the material becomes double in the length from the initial state).

FIG. 7 illustrates hardness distributions of three kinds of flexible tubes two-layer molded by each combination of resins having difference in the 100% modulus value, that is, measurement results of hardness in each position along the axial direction. About the each hardness distribution, the measurement position for measuring the hardness is shown in a distance L (cm) from a distal end 10a of the flexible tube 10 (refer to FIG. 8).

A solid line M10 is a hardness distribution of a combination of a soft resin of 2 MPa and a hard resin of 12 MPa in which the difference in the 100% modulus value is 10 MPa. A dotted line M14 is a hardness distribution of a combination of a soft resin of 2 MPa and a hard resin of 16 MPa in which the difference in the 100% modulus value is 14 MPa. These solid line M10 and dotted line M14 are the examples of the present invention that meet the condition that the difference in the 100% modulus value is equal to or more than 10 MPa.

In contrast, a chain line M6 is a hardness distribution of a combination of a soft resin of 2 MPa and a hard resin of 8 MPa in which the difference in the 100% modulus value is 6 MPa, and this is the comparative example where the difference in the 100% modulus value is less than 10 MPa.

Three kinds of the flexible tube used for the harness measurement are, for example, for an insert section of an endoscope for large intestines, and have the length of 130 cm. The outer diameter ID is 11 to 14 mm, and the thickness of the covering layer 15 is 0.2 mm to 1.0 mm. In a range to a position A of 20 cm from the distal end 10a (L=0-20 cm), the covering layer 15 is formed such that thickness of the inner layer 17: thickness of the outer layer 18 becomes 9:1, then in a range to a position B of 40 cm from the position A (L=20-60 cm), the thickness of outer layer 18 gradually increases (the thickness of inner layer 17 gradually decreases), and then in a range to a proximal end from the position B (L=60-130 cm), the covering layer 15 is formed such that thickness of the inner layer 17: thickness of the outer layer 18 becomes 1:9.

As a method for measuring the hardness of the flexible tube, as illustrated in FIG. 8, the reaction force, when both ends 10a, 10b of the flexible tube 10 are supported and the each measurement position of the flexible tube 10 along the axial direction is pushed in a predetermined amount, is measured. A numeral 50 in the figure is a hardness gauge measuring this reaction force. When the reaction force is bigger, it shows that the hardness of the part is higher.

In the solid line M10, where the difference in the 100% modulus value is 10 MPa, with respect to the position about the distal end 10a which is soft (the position A of L=20 cm), the hardness at the position about the proximal end 10b which is hard (the position C of L=120 cm) doubles.

It will be able to double the hardness at the position about the proximal end 10b with respect to the hardness at the position about the distal end 10a, by using two kinds of resins between which the difference in the 100% modulus value becomes 10 MPa for the inner layer 17 and the outer layer 18, and changing the thickness ratio of them along the axial direction.

In addition, when the difference in the 100% modulus value is 14 MPa as illustrated in the dotted line M14, with respect to the position about the distal end 10a (the position A of L=20 cm), the hardness at the position about the proximal end 10b (the position C of L=120 cm) becomes more than twice (2.4 times).

In contrast to the solid line M10 and the dotted line M14, in the chain line M6, where the difference in the 100% modulus value is 6 MPa, with respect to the position about the distal end 10a (the position A of L=20 cm), the hardness at the position about the proximal end 10b (the position C of L=120 cm) becomes less than twice (1.6 times).

To secure easy insertion of the insert section 3, with respect to the position about the distal end 10a, the hardness at the position about the proximal end 10b needs to be equal to or more than twice. This condition is required in particular in the insert section 3 for an endoscope for lower digestive tracts, which inspects a large intestine. The large intestine has many curved sections such as a sigmoid colon, whose radiuses of curvature are small, comparing to upper digestive tracts such as an esophagus or a stomach. Therefore, since an advanced maneuver is required on the insertion for the colonography, an insert section that is easier to be inserted in comparison with an endoscope for upper digestive tracts is demanded.

As illustrated in the solid line M10 and the dotted line M14, when the difference in the 100% modulus value is equal to or more than 10 MPa, it can be secured that equal to or more than the minimum necessary hardness difference (twice) between the vicinity of the distal end 10a and the vicinity of the proximal end 10b. On the other hand, as illustrated in the chain line M6, when the difference in the 100% modulus value is less than 10 MPa, the necessary hardness difference cannot be secured.

As described above, when the difference in the 100% modulus value is equal to or more than 10 MPa, the minimum necessary hardness difference can be secured. Note that, in the example of the dotted line M14, even if the thickness ratio of the inner layer 17 and the outer layer 18 is lower than the exemplified thickness ratio (for example 1.5:8.5), the minimum necessary hardness difference can be secured. Therefore, the thickness ratio of the inner layer 17 and the outer layer 18 is not a requirement to secure the minimum necessary hardness difference, and can be appropriately changed according to the difference in the 100% modulus value.

As described above, by using two kinds of resins as the inner layer 17 (the soft resin 39) and the outer layer 18 (the hard resin 40) which form the covering layer 15 of two-layers, which satisfies the two conditions that the difference of the melt viscosity in the molding temperature of 150° C. to 200° C. is equal to or less than 2500 PaS, and that the difference at the 100% modulus value is equal to or more than 10 MPa, it can be secured that both the good molding precision and the necessary hardness differences between the distal end side and the proximal end side.

In the above embodiment, the covering layer 15 is two-layer molded with the soft resin layer as the inner layer and the hard resin layer as the outer layer, but the hard resin layer can be the inner layer and the soft resin layer can be the outer layer.

In the above embodiment, the explanation is given in the example of the covering layer of two-layers, however, the covering layer may be of a multi-layered constitution having equal to or more than two-layers. In a plurality of kinds of resins used for a covering layer of the multi-layered constitution, if two kinds of resin contacting each other to be laminated are in the relation to meet the above-described two conditions, that the difference of the melt viscosity in the molding temperature of 150° C. to 200° C. is equal to or less than 2500 PaS, and that the difference at the 100% modulus value is equal to or more than 10 MPa, the same effect as in the above embodiment can be obtained. In addition, in a manufacturing process of molding a covering layer of the multi-layered constitution, at first, two kinds of resin contacting each other which are in the relation to meet the above-described two conditions are fed to a molding die heated to a predetermined molding temperature (150° C. to 200° C.), with being overlapped each other. Then, with a plurality of kinds of resins supplied to the molding die, a covering layer of the multi-layered constitution, which covers the entire peripheral surface of the axial circumference of the flexible tube material, is formed.

In the above embodiment, the explanation is given in the flexible tube constituting the insert section of the endoscope, however, also the universal cord 6 of the electronic endoscope 2 is constituted of similar flexible tube, and the present invention can be applied also to the universal cord 6.

In the above embodiment, the explanation is given in the example of the electronic endoscope for observing an image of a state of a subject body which is captured with using an imaging device, however, the present invention is not limited to this, and can be applied to an endoscope which employs an optical image guide to observe a state of a subject body.

DESCRIPTION OF THE REFERENCE NUMERALS

2 ELECTRONIC ENDOSCOPE (ENDOSCOPE)
3 INSERT SECTION
10 FLEXIBLE TUBE
14 FLEXIBLE TUBE MATERIAL

15 COVERING LAYER
17 INNER LAYER
18 OUTER LAYER
20 CONTINUOUS EXTRUSION APPARATUS (MANUFACTURING APPARATUS)
21, 22 EXTRUSION SECTION
23 HEAD SECTION
39,139 SOFT RESIN
40,140 HARD RESIN
45,145 BOUNDARY

The invention claimed is:

1. A flexible tube for an endoscope, the flexible tube comprising:
a pipe-shaped flexible tube material; and
a covering layer of a multi-layered constitution, in which an entire peripheral surface of an axis circumference of the flexible tube material is covered with a plurality of layers molded by extrusion molding, in which a plurality of kinds of resins, each having a different molten condition from each other, is supplied in an overlapped manner to one molding die to which the flexible tube material is inserted,
wherein the resin used for molding of a first layer of the covering layer and the resin used for molding of a second layer that contacts the first layer are in conditions that a difference at a 100% modulus value, which represents a hardness after molding, is equal to or more than 10 MPa, and that a difference of a melt viscosity in a temperature of 150° C. to 200° C., where the resins are molten for molding, is equal to or less than 2500 PaS,
wherein the first layer of the covering layer comprises an inner layer which covers the entire peripheral surface of the axis circumference of the flexible tube material, and the second layer comprises an outer layer which contacts the inner layer and covers the entire peripheral surface of the axis circumference of the inner layer,
wherein a thickness ratio between the inner layer and the outer layer is 1:9 at a proximal end thereof, the thickness ratio between the inner layer and the outer layer is 9:1 at a distal end thereof, and the thickness ratio reversely changes between both ends, and
wherein a thickness of the covering layer is in a range from 0.2 mm to 1.0 mm.

2. The flexible tube for the endoscope claimed in claim 1, wherein the resin used for molding the inner layer is a soft resin, and the resin used for molding the outer layer is a hard resin.

3. The flexible tube for the endoscope claimed in claim 2, wherein the flexible tube material and the covering layer are incorporated in an insert section of an endoscope.

4. The flexible tube for the endoscope claimed in claim 1, wherein a hardness around the proximal end of the flexible tube is twice or more with respect to a hardness around the distal end of the flexible tube.

5. The flexible tube for the endoscope claimed in claim 1, wherein a thickness ratio between the inner layer and the outer layer and the thickness of the covering layer are simultaneously set.

6. The flexible tube for the endoscope claimed in claim 1, wherein the thickness of the covering layer is approximately uniform in an axial direction of the flexible tube material.

7. A method for manufacturing a flexible tube for an endoscope, the method comprising:
forming a pipe-shaped flexible tube material; and
molding a covering layer of a multi-layered constitution, in which an entire peripheral surface of an axis circumference of the flexible tube material is covered with a plurality of layers molded by extrusion molding, in which a plurality of kinds of resins, each having a different molten condition each other, is supplied in an overlapped manner to one molding die to which the flexible tube material is inserted,
wherein the resin used for the molding of a first layer of the covering layer and the resin used for the molding of a second layer that contacts the first layer are in conditions that a difference at the 100% modulus value, which represents a hardness after molding, is equal to or more than 10 MPa, and that a difference of a melt viscosity in a temperature of 150° C. to 200° C., where the resins are molten for molding, is equal to or less than 2500 PaS,
wherein the first layer of the covering layer comprises an inner layer which covers the entire peripheral surface of the axis circumference of the flexible tube material, and the second layer comprises an outer layer which contacts the inner layer and covers the entire peripheral surface of the axis circumference of the inner layer,
wherein a thickness ratio between the inner layer and the outer layer is 1:9 at a proximal end thereof, the thickness ratio between the inner layer and the outer layer is 9:1 at a distal end thereof, and the thickness ratio reversely changes between the both ends, and
wherein the thickness of the covering layer is in a range from 0.2 mm to 1.0 mm.

8. The method for manufacturing a flexible tube for the endoscope claimed in claim 7, wherein the resin used for molding the inner layer comprises a soft resin, and the resin used for molding the outer layer comprises a hard resin.

9. The method for manufacturing a flexible tube for the endoscope claimed in claim 8, wherein the flexible tube material and the covering layer are incorporated in an insert section of an endoscope.

10. The method for manufacturing a flexible tube for the endoscope claimed in claim 7, wherein a hardness around the proximal end of the flexible tube is twice or more with respect to a hardness around the distal end of the flexible tube.

11. The method for manufacturing a flexible tube for the endoscope claimed in claim 7, wherein a thickness ratio between the inner layer and the outer layer and the thickness of the covering layer are simultaneously set.

12. The method for manufacturing a flexible tube for the endoscope claimed in claim 7, wherein the thickness of the covering layer is approximately uniform in an axial direction of the flexible tube material.

* * * * *